US011821033B2

(12) United States Patent
Gundlach et al.

(10) Patent No.: US 11,821,033 B2
(45) Date of Patent: Nov. 21, 2023

(54) COMPOSITIONS AND METHODS FOR IMPROVING NANOPORE SEQUENCING

(71) Applicant: University of Washington through its Center for Commercialization, Seattle, WA (US)

(72) Inventors: Jens H. Gundlach, Seattle, WA (US); Andrew Laszlo, Seattle, WA (US)

(73) Assignee: University of Washington, Seattle, WA (US)

( * ) Notice: Subject to any disclaimer, the term of this patent is extended or adjusted under 35 U.S.C. 154(b) by 372 days.

(21) Appl. No.: 17/111,167

(22) Filed: Dec. 3, 2020

(65) Prior Publication Data

US 2021/0172013 A1    Jun. 10, 2021

Related U.S. Application Data

(63) Continuation of application No. 14/419,217, filed as application No. PCT/US2013/053476 on Aug. 2, 2013, now Pat. No. 10,858,700.

(60) Provisional application No. 61/679,623, filed on Aug. 3, 2012.

(51) Int. Cl.
 *C12Q 1/6869*    (2018.01)
(52) U.S. Cl.
 CPC .................... *C12Q 1/6869* (2013.01)
(58) Field of Classification Search
 CPC ............... C12Q 1/6869; C12Q 1/6855; C12Q 2523/307; C12Q 2525/117; C12Q 2525/191; C12Q 2563/157; C12Q 2565/631; C07H 21/04
 See application file for complete search history.

(56) References Cited

U.S. PATENT DOCUMENTS

| | | | |
|---|---|---|---|
| 7,189,503 B2 | 3/2007 | Akeson | |
| 7,258,838 B2 | 8/2007 | Li | |
| 7,504,058 B1 | 3/2009 | Batten et al. | |
| 8,673,550 B2 | 3/2014 | Gundlach et al. | |
| 9,624,275 B2 | 4/2017 | Gundlach et al. | |
| 10,858,700 B2 * | 12/2020 | Gundlach | C12Q 1/6869 |
| 2011/0162963 A1 | 7/2011 | Hibbs | |
| 2011/0250705 A1 | 10/2011 | Polonsky | |
| 2011/0311965 A1 | 12/2011 | Maglia | |
| 2012/0055792 A1 | 3/2012 | Gundlach | |
| 2012/0135414 A1 * | 5/2012 | Lee | C12Q 1/6874 435/6.12 |
| 2013/0264207 A1 | 10/2013 | Ju et al. | |

FOREIGN PATENT DOCUMENTS

| | | |
|---|---|---|
| EP | 0 971 039 A2 | 1/2000 |
| EP | 1 645 628 A1 | 4/2006 |
| EP | 2 123 757 A1 | 11/2009 |
| WO | 2004/072238 A2 | 8/2004 |
| WO | 2004/087059 A2 | 10/2004 |
| WO | 2009/046094 A1 | 4/2009 |
| WO | 2010/034018 A2 | 3/2010 |
| WO | 2010/0055307 A1 | 5/2010 |
| WO | 2010/082860 A1 | 7/2010 |
| WO | WO-2010086622 A1 * | 8/2010 ............ C07H 21/04 |
| WO | 2011/106456 A2 | 9/2011 |
| WO | 2011/106459 A2 | 9/2011 |
| WO | 2011/150852 A1 | 12/2011 |
| WO | 2012/009578 A2 | 1/2012 |
| WO | 2012/058647 A1 | 5/2012 |
| WO | 2012/083249 A2 | 6/2012 |
| WO | 2013/083983 A1 | 6/2013 |

OTHER PUBLICATIONS

Bond, P.J., et al., "Molecular Dynamics Simulations of DNA Within a Nanopore: Arginine-Phosphate Tethering and a Binding/Sliding Mechanism for Translocation," Biochemistry 50(18):3777-3783, May 2011. (Author manuscript PMCID: PMC3390175, available in PMC Jul. 5, 2012, 19 pages.).

Butler, T.Z., et al., "Single-Molecule DNA Detection With an Engineered MspA Protein Nanopore," Proceedings of the National Academy of Sciences of the USA (PNAS) 105(52):20647-20652, Dec. 2008.

Cherf, G.M., et al., "Automated Forward and Reverse Ratcheting of DNA in a Nanopore at Five Angstrom Precision," National Biotechnology 30(4):344-348, Feb. 2012. (Author manuscript PMCID: PMC3408072, available in PMC Oct. 1, 2012, 14 pages.).

Chou, T., "Enhancement of Charged Macromolecule Capture by Nanopores in a Salt Gradient," Journal of Chemical Physics 131(3):034703, Jul. 2009.

Evans, D.A., et al., "The Asymmetric Synthesis of α-Amino Acids. Electrophilic Azidation of Chiral Imide Enolates, a Practical Approach to the Synthesis of (R)- and (S)-α-Azido Carboxylic Acids," Journal of the American Chemical Society 112(10):4011-4030, May 1990.

(Continued)

*Primary Examiner* — David C Thomas
(74) *Attorney, Agent, or Firm* — Christensen O'Connor Johnson Kindness PLLC (57) ABSTRACT

The present disclosure provides methods and reagents for improving nanopore-based analyses of polymers. Specifically, the disclosure provides a method of analyzing a polymer that includes a polymer analyte that contains an end domain that has at least one charged moiety. The disclosure also provides a method of increasing the interaction rate between a polymer analyte and a nanopore, wherein the polymer analyte contains an end domain that has at least one charged moiety. The disclosure also provide compositions for use with the described methods, including adapter compositions that contain charged moieties, such as phosphate or sulfate groups, and that are configured to being linked to an polymer analyte domain.

15 Claims, 3 Drawing Sheets

Specification includes a Sequence Listing.

(56) References Cited

OTHER PUBLICATIONS

Hadshiew, I.M., et al., "Stimulation of Melanogenesis by DNA Oligonucleotides: Effect of Size, Sequence and 5' Phosphorylation," Journal of Dermatological Science 25(2):127-138, Feb. 2001.

He, Y., et al., "Controlling DNA Translocation Through Gate Modulation of Nanopore Wall Surface Charges," ACS Nano 5(7):5509-5518, Jul. 2011.

International Search Report dated Oct. 8, 2013, issued in corresponding International Application No. PCT/US2013/053476, filed Aug. 2, 2013, 4 pages.

Loke, S.L., et al., "Characterization of Oligonucleotide Transport Into Living Cells," Proceedings of the National Academy of Sciences of the USA (PNAS) 86(10):3474-3478, May 1989.

Manrao, E.A., et al., "Reading DNA at Single-Nucleotide Resolution With a Mutant MspA Nanopore and phi29 DNA Polymerase," Nature Biotechnology 30(4):349-353, Apr. 2012.

Pu, Y., et al., "Synthesis and Acylation of Salts of L-Threonine B-Lactone: A Route to β-Lactone Antibiotics," Journal of Organic Chemistry 56(3):1280-1283, Feb. 1991.

Trepagnier, E.H., et al., "Controlling DNA Capture and Propagation Through Artificial Nanopores," Nano Letters 7(9):2824-2830, Sep. 2007.

Wanunu, M., "Nanopores: A Journey Towards DNA Sequencing," Physics of Life Reviews 9(2):125-158, Jun. 2012.

Williams, G.T., et al., "E1a Transactivation of the Human HSP70 Promoter Is Mediated Through the Basal Transcriptional Complex," Molecular and Cellular Biology 9(6):2574-2587, Jun. 1989.

Williams, R.M., and M.-N. Im, "Asymmetric Synthesis of Monosubstituted and α,α-Disubstituted α-Amino Acids via Diastereoselective Glycine Enolate Alkylations," Journal of the American Chemical Society 113(24):9276-9286, Nov. 1991.

Wong, C.T.A., and M. Muthukumar, "Polymer Capture by Electro-Osmotic Flow of Oppositely Charged Nanopores," Journal of Chemical Physics 126(16):164903, Apr. 2007.

Extended European Search Report dated Mar. 31, 2016, issued in corresponding Application No. EP 13825899.1, filed Aug. 2, 2013, 8 pages.

Shchepinov, M.S., "Oligonucleotide Dendrimers: From Poly-Labelled DNA Probes to Stable Nano-Structures," Glenn Report, Glen Research 12(1):1-4, Nov. 1999.

Communication Pursuant to Article 94(3) EPC dated Apr. 6, 2017, issued in corresponding European Application No. 13825899.1, filed Aug. 2, 2013, 7 pages.

Communication Pursuant to Article 94(3) EPC dated Feb. 12, 2018, issued in corresponding European Application No. 13825899.1, filed Aug. 2, 2013, 7 pages.

Examination Report No. 1 for Standard Patent Application dated Jun. 1, 2018, issued in corresponding Australian Application No. 2013296207, filed Aug. 2, 2013, 5 pages.

Communication (European Search Report) dated May 6, 2019, issued in European Application No. 18 21 3233, filed Aug. 2, 2013, 13 pages.

Kumar, S., et al., "Terminal Phosphate Labeled Nucleotides: Synthesis, Applications, and Linker Effect on Incorporation by DNA Polymerases," Nucleosides, Nucleotides and Nucleic AC, Taylor & Francis, US, 24(5-7):401-408, Jan. 2005.

Office Action dated May 7, 2019, issued in Canadian Application No. 2880274, filed Aug. 2, 2013, 5 pages.

Canadian Office Action dated May 25, 2020, issued in corresponding Canadian Application No. 2,880,274, filed Aug. 2, 2013, 4 pages.

Communication Pursuant to Article 94(3) EPC dated Sep. 7, 2020, issued in related European Patent Application No. 18213233.2, 9 pages.

Kowalska, J., et al., "Synthesis of Nucleoside Phosphosulfates," Bioorganic & Medicinal Chemistry Letters 22(11):3661-3364, Apr. 2012.

Zhou, X., et al., "Expression of Heparan Sulfate Sulfotransferases in Kluyveromyces lactis and Preparation of 3'-Phosphoadenosine-5'-Phosphosulate," Glycobiology 21(6):771-780, Jan. 2011.

Examination Report dated Sep. 16, 2020, issued in related Australian Application No. 2019200897, filed Aug. 2, 2013, 5 pages.

Examination Report No. 2 dated Jun. 22, 2023, issued in AU Application No. 2021206796, filed Aug. 2, 2013, 3 pages.

* cited by examiner

SEQUENCE LISTING

```
<160> NUMBER OF SEQ ID NOS: 3

<210> SEQ ID NO 1
<211> LENGTH: 93
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (14)..(14)
<223> OTHER INFORMATION: Wheren N at position 14 = X representing an
      abasic residue

<400> SEQUENCE: 1
aaaaaaacct tccnagacca atcaagcaac taattaagta acgaatgaag gaacaaataa      60
agaaaaccaa gcattctcat gcaggtcgta gcc                                  93

<210> SEQ ID NO 2
<211> LENGTH: 43
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (37)..(43)
<223> OTHER INFORMATION: Wherein N at positions 37-43 = X representing
      an abasic residue

<400> SEQUENCE: 2
ttggttttct ttatttgttc cttcattcgt tacttannnn nnn                       43
```

```
<210> SEQ ID NO 3
<211> LENGTH: 55
<212> TYPE: DNA
<213> ORGANISM: Artificial Sequence
<220> FEATURE:
<223> OTHER INFORMATION: Synthetic

<400> SEQUENCE: 3
gcgtacgcct acggttttcc gtaggcgtac gcggctacga cctgcatgag aatgc          55
```

COMPOSITIONS AND METHODS FOR IMPROVING NANOPORE SEQUENCING

CROSS-REFERENCE TO RELATED APPLICATION

This application is a continuation of U.S. application Ser. No. 14/419,217, filed Feb. 2, 2015, which is a National Stage of International Application No. PCT/US2013/053476, filed Aug. 2, 2013, which claims the benefit of U.S. Provisional Application No. 61/679,623, filed Aug. 3, 2012, each of which is incorporated herein by reference in its entirety.

STATEMENT OF GOVERNMENT LICENSE RIGHTS

This invention was made with Government support under R01HG005115 and R01HG006321 awarded by National Institutes of Health. The Government has certain rights in the invention.

STATEMENT REGARDING SEQUENCE LISTING

The sequence listing associated with this application is provided in text format in lieu of a paper copy and is hereby incorporated by reference into the specification. The name of the text file containing the sequence listing is 73075_Seq_final_2020-11-04.txt. The text file is 2 KB; was created on Nov. 4, 2020; and is being submitted via EFS-Web with the filing of the specification.

BACKGROUND

The rapid, reliable, and cost-effective analysis of polymer molecules, such as sequencing of nucleic acids and polypeptides, is a major goal of researchers and medical practitioners. The ability to determine the sequence of polymers, such as a nucleic acid sequence in DNA or RNA, has additional importance in identifying genetic mutations and polymorphisms. Established DNA sequencing technologies have considerably improved in the past decade but still require substantial amounts of DNA and several lengthy steps and struggle to yield contiguous readlengths of greater than 100 nucleotides. This information must then be assembled "shotgun" style, an effort that depends non-linearly on the size of the genome and on the length of the fragments from which the full genome is constructed. These steps are expensive and time-consuming, especially when sequencing mammalian genomes.

Nanopore-based analysis methods have been investigated as an alternative to traditional polymer analysis approaches. These methods involve passing a polymeric molecule, for example single-stranded DNA ("ssDNA"), through a nanoscopic opening while monitoring a signal, such as an electrical signal, that is influenced by the physical properties of the polymer subunits as the polymer analyte passes through the nanopore opening. The nanopore optimally has a size or three-dimensional configuration that allows the polymer to pass only in a sequential, single file order. Under theoretically optimal conditions, the polymer molecule passes through the nanopore at a rate such that the passage of each discrete monomeric subunit of the polymer can be correlated with the monitored signal. Differences in the chemical and physical properties of the monomeric subunits that make up the polymer, for example, the nucleotides that compose the ssDNA, result in characteristic electrical signals. Nanopores, such as for example, protein nanopores held within lipid bilayer membranes and solid state nanopores, which have been heretofore used for analysis of DNA, RNA, and polypeptides, provide the potential advantage of robust analysis of polymers even at low copy number.

However, challenges remain for the full realization of such benefits. For example, in ideal sequencing conditions, a polymer analyte must translocate linearly through the nanopore, which occurs most easily when one of the two terminal ends is captured and threaded through the nanopore. This requires an initial interaction between the terminal end of the analyte polymer with the nanopore without substantial interference from the internal portion of the polymer analyte. One challenge is presented by long polymer analytes. The likelihood of interaction between a nanopore and the terminal ends of polymers, such as nucleic acids and polypeptides, declines proportionally to the length of the polymer because of the increasing proportion of internal polymer subunits to the constant number of terminal end subunits. Furthermore, many biopolymers, such as nucleic acids and polypeptides, adopt three dimensional structures when in solution, which can often reduce the accessibility of the terminal end polymer subunits for the nanopore. Finally, biopolymers such as nucleic acids and polypeptides have an orientation (for example, DNA has a 5' terminal end and a 3' terminal end, and polypeptides have an amino terminus and carboxy terminus), such that for some applications one specific end of the polymer might be preferred over the other for initial interaction and capture by the nanopore.

Accordingly, a need remains to facilitate initial interactions between the preferred terminal end of an analyte polymer and a nanopore to facilitate efficient translocation and analysis of the analyte polymer. The methods and compositions of the present disclosure address this and related needs of the art.

SUMMARY

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

In one aspect, the present disclosure provides a method of analyzing a polymer. The method comprises applying an electric field sufficient to translocate the polymer through a nanopore and measuring an ion current to provide a current pattern. The polymer comprises an analyte domain and an end domain, wherein the end domain has a first charged moiety. In some embodiments, the electric field is sufficient to translocate the polymer through a nanopore, from a first conductive liquid medium to a second conductive liquid medium. A difference in the ion current from the threshold amount in the current pattern indicates a characteristic of the analyte polymer.

In some embodiments, the polymer comprises DNA, RNA, PNA, a polypeptide, or a combination thereof. In some embodiments, the polymer end domain is a contiguous domain that consists of 50% or fewer of the total polymer subunits including one of the end subunits. In some embodiments, the polymer end domain is a contiguous domain consisting of 1 to 10 polymer subunits including one of the end subunits of the polymer.

In some embodiments, the charged moiety results in an end domain that is more charged than the average charge density of the polymer. In some embodiments, the charged moiety results in an end domain that is less charged than the average charge density of the polymer. In some embodiments, the charged moiety results in an end domain that has the opposite charge as the average charge density of the polymer. In some embodiments, the charged moiety has a net positive charge. In some embodiments, the charged moiety with a net positive charge comprises one of a charged amino acid, modified charged nucleotide, and a basic residue forming a cation. In some embodiments, the charged moiety has a net negative charge. In some embodiments, the charged moiety with a net negative charge comprises one of a phosphate, sulfate, charged amino acid, modified charged nucleotide, and an acidic residue forming an anion. In some embodiments, the nanopore comprises a vestibule with a net charge that is opposite to the net charge of the first charged moiety.

In some embodiments, the nanopore is a solid-state nanopore, protein nanopore, hybrid solid state-protein (or biological) nanopore, biologically adapted solid state pore, or a DNA origami nanopore. In some embodiments, the nanopore is a protein nanopore selected from alpha-hemolysin or *Mycobacterium smegmatis* porin A (MspA), or a homolog thereof. In some embodiments, the protein nanopore sequence is modified to contain at least one amino acid substitution, deletion, or addition. In some embodiments, the at least one amino acid substitution, deletion, or addition results in a net charge change in the nanopore. In some embodiments, the net charge change decreases the similarity of charge with the first charged moiety (i.e., increases the charge difference).

In some embodiments, the polymer analyte further comprises a second end domain at the opposite end of the polymer analyte from the first end domain, wherein the second end domain comprises a second charged moiety that has a charge opposed to the charge of the first charged moiety. In some embodiments, the polymer comprises DNA with the end domain comprising the 5' end subunit of the DNA, and wherein the first charged moiety is a phosphate. In further embodiments, the method also comprises adding a positively charged moiety to the 3' end domain of the DNA. In other embodiments, the polymer comprises DNA with the end domain comprising the 3' end subunit of the DNA, and wherein the first charged moiety is a phosphate. In further embodiments, the method also comprises adding a positively charged moiety to the 5' end domain of the DNA.

In some embodiments, the electric field is between about 40 mV to 1 V.

In some embodiments, the nanopore is associated with a molecular motor, wherein the molecular motor is capable of moving an analyte into or through the nanopore with an average translocation velocity that is less than the average translocation velocity at which the analyte electrophoretically translocates into or through the nanopore in the absence of the molecular motor. In some embodiments, the characteristic of the analyte polymer is the presence of the analyte polymer. In some embodiments, the characteristic of the analyte polymer is the identity of at least one subunit of the analyte domain. In some embodiments, a difference in the current from a reference current defines a blockade in the current pattern for the at least one subunit of the analyte domain. Identifying the at least one subunit comprises comparing the one or more blockades in the current pattern to one or more blockades in a known current pattern obtained using a known analyte.

In another aspect, the disclosure provides a method of increasing the interaction rate between a polymer and a nanopore disposed between a first conductive liquid medium and a second conductive liquid medium. The method comprises applying an electric field sufficient to translocate a polymer from the first conductive liquid medium to the second conductive liquid medium through the nanopore. The method further comprises measuring an ion current to provide a current pattern. The polymer has an analyte domain and an end domain. The end domain comprises a first charged moiety. A difference in the ion current from a threshold ion current level in the current pattern indicates an interaction between the polymer and the nanopore.

In some embodiments, the polymer comprises DNA, RNA, PNA, a polypeptide, or a combination thereof. In some embodiments, the end domain comprises between 1 and 10 polymer subunits including an end subunit.

In some embodiments, the first charged moiety has a net positive charge. In some embodiments, the first charged moiety has a net negative charge.

In some embodiments, the nanopore comprises a vestibule with a net charge that is opposite the net charge of the first charged moiety.

In some embodiments, the interaction rate between the nanopore and the polymer is at least 10%, 20%, 30%, 40%, 50%, 60%, 70%, 80%, 90%, 100%, 150%, or 200% higher than the interaction rate between the nanopore and the polymer lacking the first charged moiety in the end domain.

In another aspect, the disclosure provides a polymer adapter composition. The adapter composition comprises a polynucleic acid with between 1 and 20 nucleotides, and a charged moiety linked to at least one of the nucleotides of the polynucleic acid. In this aspect, the charged moiety comprises at least two phosphate and/or sulfate groups.

In some embodiments, the charged moiety is covalently linked to the at least one nucleotide. In some embodiments, the charged moiety is ionically linked to the at least one nucleotide. In some embodiments, the charged moiety is indirectly linked to the at least one nucleotide.

In some embodiments, the phosphate and/or sulfate groups are disposed in linear or branched configuration. In some embodiments, the phosphate and/or sulfate groups are disposed in a branched configuration with two or more charged groups in each branch.

In another aspect, the present disclosure provides a kit nanopore-based polymer sequencing, comprising the disclosed adapter composition. In some embodiments, the kit also comprises reagents for ligating the adapter to a polymer analyte domain. In some embodiments, the kit also comprises components to assemble a nanopore system.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein:

FIG. 1A illustrates a DNA analyte (SEQ ID NO:1), with indicated domains that hybridize to a blocking oligo (SEQ ID NO:2) and a domain of a hairpin oligo (SEQ ID NO:3). The blocking oligo (SEQ ID NO:2) as illustrated has an "abasic fray" domain at the 3' end with seven contiguous abasic residues (each illustrated with an "X") and a carbon spacer (illustrated with a "Z"). Arrows are included to indicate the how the domains of the various polynucleic acids hybridize with each other. FIG. 1B illustrates the DNA analyte polymer as it is hybridized to the blocking and hairpin oligos. The hairpin oligo has a loop domain consisting of TTTT, two complementary hairpin domains that hybridize to each other, and a domain that hybridizes to the 3' end of the DNA analyte polymer. The blocking oligo hybridizes to the DNA analyte polymer starting after the 3' end of the hairpin oligo, but without being linked to the hairpin oligo. The abasic fray domain of the blocking oligo is shown as not hybridizing with the analyte sequence. This configuration of DNA analyte polymer and oligos can be used in conjunction with a nanopore system incorporating a molecular motor, such as phi29, as described herein.

DETAILED DESCRIPTION

The present disclosure generally relates to compositions and methods to efficiently analyze polymer characteristics where interactions between the analyte polymer and a nanopore are required. In some aspects, the present disclosure relates to compositions and methods that improve the interaction rate between the polymer analyte and the nanopore.

Nanopores hold promise for inexpensive, fast, and nearly "reagent-free" analysis of polymers. In a general embodiment of a nanopore system, an external voltage is applied across a nanometer-scale, electrolyte-filled pore, inducing an electric field. Any analyte, such as a polymer that contacts, resides in, or moves through, the interior of the pore, modulates the ionic current that passes through the pore depending on its physical characteristics. If the interior tunnel formed by the pore is of sufficiently small diameter and length, polymers that pass through must pass in a linear fashion, such that only a subset of the polymer subunits reside in the most constricted zone of the pore tunnel at one time. Thus, the ionic current fluctuates over time as the polymer passes through the nanopore, subunit by subunit, depending on the different physical characteristics of the subunit(s) residing in the nanopore constriction zone at each iterative step.

As described above, a major challenge for nanopore-based analysis of polymers is establishing an appropriate initial interaction between the polymer analyte and nanopore to facilitate capture of the appropriate terminal end of the polymer analyte and the subsequent passage of the polymer through the nanopore in a linear fashion. With increasing polymer length, the accessibility of a terminal end of a polymer to the nanopore, as opposed to an internal portion of the polymer, decreases because of the increasing proportion of internal bulk of the polymer. This reduced accessibility, especially in situations with low analyte copy number, makes the establishment of an appropriate initial interaction between the polymer analyte end and the nanopore very difficult.

The present inventors have developed an approach to improve the appropriate interaction rate between a polymer analyte and the nanopore to facilitate analysis in a nanopore-based analysis system. The improved interaction rate results in improved capture rates of the polymer, and thus, improved analysis conditions and results. As described in more detail below, the inventors have developed methods and compounds that increase the charge at one or more ends of the analyte polymer. Charging the ends of the polymer analyte increases the energetic favorability for the preferred end of the polymer to interact with, and be captured by, the nanopore for analysis. To illustrate, the inventors modified the 5' ends of single strand DNA with a variety of phosphate groups in different configurations, as described in more detail below. The DNA analytes were subjected to comparative analysis in a nanopore system that specifically incorporated a modified *Mycobacterium smegmatis* porin A (MspA) nanopore. The analytes with additions of the charged phosphate groups demonstrated remarkably improved interaction and capture rates over the unmodified DNA analyte, resulting in a markedly increased efficiency for the analysis.

In accordance with the foregoing, in one aspect, the present disclosure provides a method of analyzing a polymer. The method comprises applying an electric field sufficient to translocate the polymer through a nanopore from a first conductive liquid medium to a second conductive liquid medium, wherein the polymer comprises an analyte domain and an end domain, wherein the end domain has a first charged moiety. In some embodiments, the method also comprises measuring an ion current to provide a current pattern, wherein a reduction in the ion current below a threshold ion current level in the current pattern indicates a characteristic of the analyte polymer.

The present invention encompasses methods and compounds to facilitate the analysis of any polymer analyte amendable to analysis in a nanopore-based system. As used herein, the term "polymer" refers to a chemical compound comprising two or more repeating structural units, referred to herein interchangeably as "subunits," "monomeric units," or "mers," where each subunit can be the same or different. Nonlimiting examples of polymers to be analyzed with the present methods include: nucleic acids, peptides, and proteins, as well as a variety of hydrocarbon polymers (e.g., polyethylene, polystyrene) and functionalized hydrocarbon polymers, wherein the backbone of the polymer comprises a carbon chain (e.g., polyvinyl chloride, polymethacrylates). Polymers include copolymers, block copolymers, and branched polymers such as star polymers and dendrimers.

In some embodiments, the polymer is or comprises a nucleic acid. The term "nucleic acid" refers to a deoxyribonucleotide polymer (DNA) or ribonucleotide polymer (RNA) in either single- or double-stranded form. The structure of the canonical polymer subunits of DNA, for example, are commonly known and are referred to herein as adenine (A), guanine (G), cytosine (C), and thymine (T). As a group, these are generally referred to herein as nucleotides or nucleotide residues. For RNA, the 20 canonical polymer subunits are the same, except with uracil (U) instead of thymine (T).

In some embodiments, the polymer is or comprises a polypeptide, i.e., the polymer is or comprises a sequence of amino acid residues. As used herein, an "amino acid" refers to any of the 20 naturally occurring amino acids found in proteins, D-stereoisomers of the naturally occurring amino acids (e.g., D-threonine), unnatural amino acids, and chemically modified amino acids. Each of these types of amino acids is not mutually exclusive. α-Amino acids comprise a carbon atom to which is bonded an amino group, a carboxyl group, a hydrogen atom, and a distinctive group referred to as a "side chain." The side chains of naturally occurring amino acids are well known in the art and include, for example, hydrogen (e.g., as in glycine), alkyl (e.g., as in alanine, valine, leucine, isoleucine, proline), substituted alkyl (e.g., as in threonine, serine, methionine, cysteine, aspartic acid, asparagine, glutamic acid, glutamine, arginine, and lysine), arylalkyl (e.g., as in phenylalanine and tryptophan), substituted arylalkyl (e.g., as in tyrosine), and heteroarylalkyl (e.g., as in histidine).

The following abbreviations are used for the 20 naturally occurring amino acids: alanine (Ala; A), asparagine (Asn; N), aspartic acid (Asp; D), arginine (Arg; R), cysteine (Cys; C), glutamic acid (Glu; E), glutamine (Gln; Q), glycine (Gly; G), histidine (His; H), isoleucine (Ile; I), leucine (Leu; L), lysine (Lys; K), methionine (Met; M), phenylalanine (Phe; F), proline (Pro; P), serine (Ser; S), threonine (Thr; T), tryptophan (Trp; W), tyrosine (Tyr; Y), and valine (Val; V).

Any of the foregoing examples of polymers can also include noncanonical subunits or analogs. Noncanonical subunits can be useful to provide an obvious output signal to indicate that the end of a reference domain has passed through the nanopore. Regarding embodiments of nucleic acid polymers, illustrative and nonlimiting examples of noncanonical subunits include uracil (for DNA), 5-methyl-cytosine, 5-hydroxymethylcytosine, 5-formethylcytosine, 5-carboxycytosine b-glucosyl-5-hydroxy-methylcytosine, 8-oxoguanine, 2-amino-adenosine, 2-amino-deoxyadenosine, 2-thiothymidine, pyrrolo-pyrimidine, 2-thiocytidine, or an abasic lesion. An abasic lesion is a location along the deoxyribose backbone but lacking a base. Known analogs of natural nucleotides hybridize to nucleic acids in a manner similar to naturally occurring nucleotides, such as peptide nucleic acids (PNAs) and phosphorothioate DNA.

Representative noncanonical peptide residues are known in the art, as set forth in, for example, Williams et al., *Mol. Cell. Biol.* 9:2574 (1989); Evans et al., *J. Amer. Chem. Soc.* 112:4011-4030 (1990); Pu et al., *J. Amer. Chem. Soc.* 56:1280-1283 (1991); Williams et al., *J. Amer. Chem. Soc.* 113:9276-9286 (1991); and all references cited therein. Exemplary noncanonical amino acids include, but are not limited to: 2-Aminoadipic acid, N-Ethylasparagine, 3-Aminoadipic acid, Hydroxylysin, β-alanine, β-Amino-propionic acid, allo-Hydroxylysine, 2-Aminobutyric acid, 3-Hydroxyproline, 4-Aminobutyric acid, piperidinic acid, 4-Hydroxyproline, 6-Aminocaproic acid, Isodesmosine, 2-Aminoheptanoic acid, allo-Isoleucine, 2-Aminoisobutyric acid, N-Methylglycine, sarcosine, 3-Aminoisobutyric acid, N-Methylisoleucine, 2-Aminopimelic acid, 6-N-Methyllysine, 2,4-Diaminobutyric acid, N-Methylvaline, Desmosine, Norvaline, 2,2'-Diaminopimelic acid, Norleucine, 2,3-Diaminopropionic acid, Ornithine, N-Ethylglycine. Methods of incorporating noncanonical amino acids are well known in the art.

In some embodiments, a single polymer analyte can comprise a combination of any of the foregoing polymers and/or polymer subunits. For example, in some embodiments, the polymer analyte is a combination of any two or more of DNA, RNA, PNA, and or polypeptide.

Additionally, in some embodiments, the polymer analyte can contain modifications to one or more of the polymer subunits. In some embodiments, the modified analyte comprises a modified nucleic acid or modified amino acid. In some embodiments, the modified nucleic acid comprises a modified DNA, a modified RNA, a modified PNA, or a combination thereof. Such modifications, and their implementation in polymers, are commonly known in the art and can facilitate the analysis of the polymer analytes.

The polymer can be characterized as comprising an analyte domain and at least one end domain. The "analyte domain" is the portion of the polymer analyte that is to be characterized in some way by the nanopore analysis. For example, the presence of an identifiable characteristic, such as a "fingerprint," sequence pattern, or actual primary sequence of various subunits thereof, can be identified in the analyte domain. In some embodiments, the mere presence of the analyte domain, i.e., the presence of one or more polymer subunits excluding the end domain, is confirmed in the analysis. In some embodiments, the primary sequence (i.e., identity) of two or more polymer subunits in the analyte domain is determined. Additional description of how the analyte domain is characterized in a nanopore system is provided below.

The "end domain" is a portion of the polymer that comprises at least one charged moiety. The moiety is linked to the polymer at one of the terminal ends of the polymer. The term "terminal end" is used herein to indicate a portion of the polymer comprising a terminal polymer subunit. The term "terminal subunit" is used herein to indicate a polymer subunit that is only linked to one other polymer subunit, as opposed to an "interior" subunit, which is linked to at least two additional subunits (e.g., linked to one subunit on each side, for an interior subunit in a linear polymer.) Accordingly, a linear polymer will have two terminal ends, and thus two terminal end subunits, at opposite ends of the polymer. In some embodiments, a terminal end can comprise the terminal-most 2, 3, 4, 5, 6, 7, 8, 9, 10, 11, 12, 13, 14, 15, 16, 17, 18, 19, or 20 polymer subunits, including a terminal end subunit. Thus, for example, the end domain can be at least one charged moiety linked to any one of the polymer subunits in one of the terminal ends, as recited above. In some embodiments the terminal end of the polymer is defined as a contiguous domain of polymer subunits consisting of 60% or fewer of the total subunits of the polymer and including one of the terminal subunits, such as 60%, 55%, 50%, 45%, 40%, 35%, 30%, 25%, 20%, 15%, 10%, 5%, 4%, 3%, 2%, 1%, or any percent therein, or fewer of the total subunits of the polymer, including one of the terminal subunits.

In some embodiments, the end domain consists of the at least one charged moiety, with the proviso that it is linked to the polymer at one of the terminal ends of the polymer.

In other embodiments, the end domain comprises the at least one charged moiety, and also comprises at least one of the polymer subunits. In some embodiments, the end domain comprises one of the terminal subunits of the polymer and at least one charged moiety. In some embodiments, the end domain comprises a plurality of contiguous polymer subunits including one of the end subunits of the polymer. For example, the terminal end domain can comprise the last 2, 3, 4, 5, 6, 7, 8, 9, 10, 11, 12, 13, 14, 15, 16, 17, 18, 19, or 20 polymer subunits, including a terminal end subunit and at least one charged moiety. In some embodiments, the terminal end domain comprises a contiguous domain of polymer subunits consisting of 20% or fewer of the total subunits of the polymer and including one of the terminal subunits and the at least one charged moiety.

As used herein, the term "charged moiety" means any chemical structure or substructure that provides an electrical charge, either positive or negative, resulting from a deficit or excess of electrons relative to the protons in the structure or substructure. In some embodiments, the charged moiety, or the end domain including the charged moiety, has a net positive charge. In some embodiments, the charged moiety, or the end domain including the charged moiety, has a net negative charge. In some circumstances, it is useful to consider the net charge of the end domain in relation to other components of the polymer. Thus, in some embodiments, the charged moiety results in an end domain that is more charged as compared to the average charge density of the polymer. For example, DNA is generally negatively charged and has an average negative charge density per nucleotide residue within the polymer. The addition of a negatively charged moiety at the end domain of the DNA polymer results in a greater negative charge at the location of attachment (i.e., indicating a further excess of electrons) as compared to the average charge density of nucleotides in the rest of the DNA polymer. In other embodiments, the charged moiety results in an end domain that is less charged, as compared to the average charge density of the polymer. For example, with the illustrative DNA polymer described above, the addition of a positively charged moiety at the end domain of the DNA polymer results in a lesser negative charge, or even a positive charge, at the location of attachment (i.e., indicating a lesser excess of electrons, or a relative deficit of electrons) as compared to the average charge density of nucleotides in the rest of the DNA polymer.

Some polymer analytes contain structurally different ends, resulting in a discernable orientation with respect to passage through the nanopore. For example, DNA has a 5' end and a 3' end. Alternatively, polypeptides have an amino terminus and a carboxy terminus. Accordingly, a charged moiety and/or end domain, as described herein, can be strategically added to a specific end of the analyte polymer. Thus, depending on the relative charges of the polymer end(s) and the nanopore, the initial interaction, capture, and translocation of the polymer analyte can be made much more energetically favorable for one of the two polymer ends, thus promoting a preferred orientation with respect to interactions with the nanopore.

Accordingly, in some embodiments, the charged moiety, or the end domain including the charged moiety, has a net charge that is opposite of the net charge on the opening or vestibule of the nanopore. The nanopore structure, including the vestibule, is described in more detail below. In some embodiments, the charged moiety, or the end domain including the charged moiety, has a net positive charge, whereas the nanopore opening or vestibule has a net negative charge. Alternatively, in some embodiments, the charged moiety, or the end domain including the charged moiety, has a net negative charge, whereas the nanopore opening or vestibule has a net positive charge. With opposing charges, the interaction between the end domain and the nanopore opening or vestibule becomes much more energetically favorable. Furthermore, in embodiments where the net charge of the end domain is greater than the average density charge of the remaining portions of the polymer, the end domain is more likely to disassociate from the three-dimensional structures that often form with long polymers. Accordingly, the end domain is more accessible to the nanopore opening or vestibule.

In some embodiments, the charged moiety, or the end domain including the charged moiety, has a net charge that is the same as the net charge on the opening or vestibule of the nanopore. For example, in some embodiments, the charged moiety, or the end domain including the charged moiety, and the nanopore opening or vestibule have a net positive charge. Alternatively, in some embodiments, the charged moiety, or the end domain including the charged moiety, and the nanopore opening or vestibule have a net positive charge. With the same net charges, the interaction between the end domain and the nanopore opening or vestibule becomes much less energetically favorable. Consequently, any interaction between the nanopore and an analyte end will more likely favor the end that does not have the charged moiety with the same net charge as the nanopore. Furthermore, in embodiments where the net charge of the end domain is less than (or opposite of) the average density charge of the remaining portions of the polymer, the end domain is more likely to associate with the three-dimensional structures that often form with long polymers. Accordingly, the end domain is made less accessible to the nanopore opening or vestibule. Again, this can result in favoring an initial interaction and capture between the polymer end that does not have the charged moiety with the same net charge as the nanopore.

In some embodiments, the polymer analyte further comprises a second end domain that comprises a second charged moiety. For example, in linear polymers the second end domain is located at the opposite end of the polymer from the first end domain. In some embodiments, the second charged moiety has a charge that is opposite of the first charged moiety, thus resulting in a polarized polymer with one positively charged end domain and one negatively charged end domain. As with the charged moiety described above (i.e., the "first" charged moiety), the second charged moiety is linked to the polymer at a terminal end of the polymer. Having a polarized polymer analyte can further promote the preferred orientation of the polymer with respect to interaction with, and translocation through, the nanopore. In an example incorporating a nanopore with a net positive charge on the vestibule, a DNA analyte can comprise a first end domain with a negative moiety at the 5' end to promote the capture of that end by the nanopore. Additionally, the same DNA analyte can further comprise a second end domain at the 3' end with a positively-charged moiety, which serves to further promote the capture of the 5' end by the nanopore. It will be understood that if the preferred orientation is to have the 3' end first enter the nanopore, the charges at the end domains can be reversed from that described above, with the 3' end domain having a negatively charged moiety and the 5' end domain having a positively charged moiety.

Examples of chemical structures that can serve as positively charged moieties in accordance with the present invention are well-known in the art. An illustrative and nonlimiting list includes: charged amino acid, basic residues forming a cation, and the like.

Examples of chemical structures that can serve as negatively charged moieties in accordance with the present invention are well-known in the art. An illustrative and nonlimiting list includes: phosphate, sulfate, charged amino acid, modified charged nucleotide, acidic residue forming an anion, and the like.

In some embodiments, the charged moiety can comprise multiple copies of any of the compounds described herein. This has the advantage of increasing the desired charge to be incorporated into the end domain of the polymer. The multiple copies can be covalently linked in any configuration that does not prevent the entire moiety from being attached to the end domain. For example, as described in more detail below, multiple phosphate groups were attached to the end of a single stranded DNA domain in linear, branched (also referred to as "doubler"), and a combination thereof (such as a doubler with each branch containing one or more multiple phosphate groups in linear configuration; and a "stacked doubler," where each of two primary branches leads to an additional branching, resulting in four phosphate groups). See, e.g., FIG. 2. To generate the branched, or doubler, configuration, an asymmetric doubler can be used, according to methods known in the art (see, e.g., http://www.glenresearch.com/GlenReports/GR12-11.html). Doubler and even trebler configurations are readily available as phosphoramidite synthons that can be used in standard oligomer synthesis techniques widely known in the art. For example, DNA adapters can be ligated onto the desired analytes using known techniques.

Various aspects of the nanopore and nanopore system will now be described. A "nanopore" specifically refers to a pore having an opening with a diameter at its most narrow point of about 0.3 nm to about 2 nm. Nanopores useful in the present disclosure include any pore capable of permitting the linear translocation of a polymer from one side to the other at a velocity amenable to monitoring techniques, such as techniques to detect current fluctuations. In some embodiments, the nanopore comprises a protein, such as alpha-hemolysin, *Mycobacterium smegmatis* porin A (MspA), OmpATb, homologs thereof, or other porins, as described in U.S. Pub. No. US2012/0055792, International PCT Pub. Nos. WO2011/106459, and WO2011/106456, incorporated herein by reference in their entireties. A "homolog," as used herein, is a gene from another bacterial species that has a similar structure and evolutionary origin. By way of an example, homologs of wild-type MspA, such as MppA, PorM1, PorM2, and Mmcs4296, can serve as the nanopore in the present invention. Protein nanopores have the advantage that, as biomolecules, they self-assemble and are essentially identical to one another. In addition, it is possible to genetically engineer protein nanopores to confer desired attributes, such as substituting amino acid residues for amino acids with different charges, or to create a fusion protein (e.g., an exonuclease+alpha-hemolysin). Thus, the protein nanopores can be wild-type or can be modified to contain at least one amino acid substitution, deletion, or addition. In some embodiments the at least one amino acid substitution, deletion, or addition results in a different net charge of the nanopore. In some embodiments, the different in net charge increases the difference of net charge as compared to the first charged moiety of the polymer analyte. For example, if the first charged moiety has a net negative charge, the at least one amino acid substitution, deletion, or addition results in a nanopore that is less negatively charged. In some cases, the resulting net charge is negative (but less so), is neutral (where it was previously negative), is positive (where is was previously negative or neutral), or is more positive (where it was previously positive but less so).

Descriptions of modifications to MspA nanopores have been described, see U.S. Pub. No. 2012/0055792, incorporated herein by reference in its entirety. Briefly described, MspA nanopores can be modified with amino acid substitutions to result in a MspA mutant with a mutation at position 93, a mutation at position 90, position 91, or both positions 90 and 91, and optionally one or more mutations at any of the following amino acid positions: 88, 105, 108, 118, 134, or 139, with reference to the wild type amino acid sequence. In one specific embodiment, the MspA contains the mutations D90N/D91N/D93N, with reference to the wild type sequence positions (referred to therein as "M1MspA" or "M1-NNN"). In another embodiment, the MspA contains the mutations D90N/D91N/D93N/D118R/D134R/E139K, with reference to the wild type sequence positions (referred to therein as "M2MspA"). See U.S. Pub. No. 2012/0055792. Such mutations can result in a MspA nanopore that comprises a vestibule having a length from about 2 to about 6 nm and a diameter from about 2 to about 6 nm, and a constriction zone having a length from about 0.3 to about 3 nm and a diameter from about 0.3 to about 3 nm, wherein the vestibule and constriction zone together define a tunnel. Furthermore, the amino acid substitutions described in these examples provide a greater net positive charge in the vestibule of the nanopore, further enhancing the energetic favorability of interacting with a negatively charged analyte polymer end.

In some embodiments, the nanopores can include or comprise DNA-based structures, such as generated by DNA origami techniques. For descriptions of DNA origami-based nanopores for analyte detection, see PCT Pub. No. WO2013083983, incorporated herein by reference.

In some embodiments, the nanopore can be a solid state nanopore. Solid state nanopores can be produced as described in U.S. Pat. Nos. 7,258,838 and 7,504,058, incorporated herein by reference in their entireties. Solid state nanopores have the advantage that they are more robust and stable. Furthermore, solid state nanopores can in some cases be multiplexed and batch fabricated in an efficient and cost-effective manner. Finally, they might be combined with micro-electronic fabrication technology. In some embodiments, the nanopore comprises a hybrid protein/solid state nanopore in which a nanopore protein is incorporated into a solid state nanopore. In some embodiments, the nanopore is a biologically adapted solid-state pore.

In some embodiments, such as incorporating MspA protein nanopores, the nanopore comprises a vestibule and a constriction zone that together form a tunnel. A "vestibule" refers to the cone-shaped portion of the interior of the nanopore whose diameter generally decreases from one end to the other along a central axis, where the narrowest portion of the vestibule is connected to the constriction zone. A vestibule may generally be visualized as "goblet-shaped." Because the vestibule is goblet-shaped, the diameter changes along the path of a central axis, where the diameter is larger at one end than the opposite end. The diameter may range from about 2 nm to about 6 nm. Optionally, the diameter is about, at least about, or at most about 2, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, or 6.0 nm, or any range derivable therein. The length of the central axis may range from about 2 nm to about 6 nm. Optionally, the length is about, at least about, or at most about 2, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, or 6.0 nm, or any range derivable therein. When referring to "diameter" herein, one can determine a diameter by measuring center-to-center distances or atomic surface-to-surface distances.

A "constriction zone" refers to the narrowest portion of the tunnel of the nanopore, in terms of diameter, that is connected to the vestibule. The length of the constriction zone can range, for example, from about 0.3 nm to about 20 nm. Optionally, the length is about, at most about, or at least about 0.3, 0.4, 0.5, 0.6, 0.7, 0.8, 0.9, 1.0, 1.1, 1.2, 1.3, 1.4, 1.5, 1.6, 1.7, 1.8, 1.9, 2, or 3 nm, or any range derivable therein. The diameter of the constriction zone can range from about 0.3 nm to about 2 nm. Optionally, the diameter is about, at most about, or at least about 0.3, 0.4, 0.5, 0.6, 0.7, 0.8, 0.9, 1.0, 1.1, 1.2, 1.3, 1.4, 1.5, 1.6, 1.7, 1.8, 1.9, 2, or 3 nm, or any range derivable therein. In other embodiment, such as those incorporating solid state pores, the range of dimension (length or diameter) can extend up to about 20 nm. For example, the constriction zone of a solid state nanopore is about, at most about, or at least about 0.3, 0.4, 0.5, 0.6, 0.7, 0.8, 0.9, 1.0, 1.1, 1.2, 1.3, 1.4, 1.5, 1.6, 1.7, 1.8, 1.9, 2, 3, 4, 5, 6, 7, 8, 9, 10, 11, 1, 2 13, 14, 15, 16, 17, 18, 19, or 20 nm, or any range derivable therein. Larger dimension in such nanopores can be preferable depending on the In some cases, the nanopore is disposed within a membrane, thin film, or lipid bilayer, which can separate the first and second conductive liquid media, which provides a nonconductive barrier between the first conductive liquid medium and the second conductive liquid medium. The nanopore, thus, provides liquid communication between the first and second conductive liquid media. In some embodiments, the pore provides the only liquid communication between the first and second conductive liquid media. The liquid media typically comprises electrolytes or ions that can flow from the first conductive liquid medium to the second conductive liquid medium through the interior of the nanopore. Liquids employable in methods described herein are well-known in the art. Descriptions and examples of such media, including conductive liquid media, are provided in U.S. Pat. No. 7,189,503, for example, which is incorporated herein by reference in its entirety. The first and second liquid media may be the same or different, and either one or both may comprise one or more of a salt, a detergent, or a buffer. Indeed, any liquid media described herein may comprise one or more of a salt, a detergent, or a buffer. Additionally, any liquid medium described herein may comprise a viscosity-altering substance or a velocity-altering substance.

The analyte polymer serving as the target or focus of an analysis is capable of interacting with the nanopore and translocating, preferably in a linear fashion, through the pore to the other side. As used herein, the terms "interact" or "interacting," indicate that the analyte moves into at least an interior portion of the nanopore and, optionally, moves through the nanopore. As used herein, the terms "through the nanopore" or "translocate" are used to convey for at least some portion of the polymer analyte to enter one side of the nanopore and move to and out of the other side of the nanopore. In some cases, the first and second conductive liquid media located on either side of the nanopore are referred to as being on the cis and trans regions, where the analyte polymer to be measured generally translocates from the cis region to the trans region through the nanopore. However, in some embodiments, the analyte polymer to be measured can translocate from the trans region to the cis region through the nanopore. In some cases, the entire length of the polymer does not pass through the pore, but portions or segments of the polymer pass through the nanopore for analysis.

The analyte polymer can be translocated through the nanopore using a variety of mechanisms. For example, the analyte polymer and/or reference sequence can be electrophoretically translocated through the nanopore. Nanopore systems also incorporate structural elements to apply an electrical field across the nanopore-bearing membrane or film. For example, the system can include a pair of drive electrodes that drive current through the nanopores. Additionally, the system can include one or more measurement electrodes that measure the current through the nanopore. These can be, for example, a patch-clamp amplifier or a data acquisition device. For example, nanopore systems can include an Axopatch-1B patch-clamp amplifier (Axon Instruments, Union City, CA) to apply voltage across the bilayer and measure the ionic current flowing through the nanopore. The electrical field is sufficient to translocate a polymer analyte through the nanopore. As will be understood, the voltage range that can be used can depend on the type of nanopore system being used. For example, in some embodiments, the applied electrical field is between about 20 mV and about 260 mV, for protein-based nanopores embedded in lipid membranes. In some embodiments, the applied electrical field is between about 40 mV and about 200 mV. In some embodiments, the applied electrical field is between about 100 mV and about 200 mV. In some embodiments, the applied electrical field is about 180 mV. In other embodiments where solid state nanopores are used, the applied electrical field can be in a similar range as described, up to as high as 1 V.

Additionally or alternatively, nanopore systems can include a component that translocates a polymer through the nanopore enzymatically. For example, a molecular motor can be included to influence the translocation of polymers through the nanopore. A molecular motor can be useful for facilitating entry of a polymer into the nanopore and/or facilitating or modulating translocation of the polymer through the nanopore. Ideally, the translocation velocity, or an average translocation velocity, is less than the translocation velocity that would occur without the molecular motor. In any embodiment herein, the molecular motor can be an enzyme, such as a polymerase, an exonuclease, or a Klenow fragment. In one example, described in more detail below, a DNA polymerase such as phi29 can be used to facilitate movement in both directions. See Cherf, G. M., et al., "Automated forward and reverse ratcheting of DNA in a nanopore at 5-A precision," *Nat. Biotechnol.* 30:344-348 (2012), and Manrao et al., "Reading DNA at single-nucleotide resolution with a mutant MspA nanopore and phi29 DNA polymerase," *Nat. Biotechnol.* 30:349-353 (2012), both of which are incorporated herein by reference in their entireties.

As described above, the "analyte domain" is the portion of the polymer analyte that is to be characterized in some way by the nanopore analysis. Typically, the analyte domain is the portion of the polymer analyte that is not part of the end domain. However, in some embodiments characteristics of the end domain (if comprising polymer subunits) are determined, in addition to determining characteristics of the analyte domain. Characteristics of an analyte domain, or subunits thereof, can be determined in a nanopore system based on measurable effects of their residency in the nanopore. In some embodiments, the mere presence of the analyte domain, i.e., the presence of one or more polymer subunits, excluding the end domain, is confirmed in the analysis. In some embodiments, additional information is determined about the one or more polymer subunits in the analyte domain. In some embodiments, the presence of an identifiable characteristic, such as a "fingerprint" or primary subunit sequence, is identified in the analyte domain. In some embodiments, the sequence identity is determined for one, two, or more polymer subunits in the analyte domain. In some embodiments, the sequence of the analyte domain is determined.

Characteristics of the analyte domain, or subunit(s) thereof, can be determined based on the effect of the analyte domain, or subunit(s) thereof, on a measurable signal when interacting with the nanopore, such as interactions with the outer rim, vestibule, or constriction zone of the nanopore. To illustrate, in some embodiments, the polymer subunit(s) that determine(s) or influence(s) a measurable signal is/are the subunit(s) residing in the "constriction zone," i.e., the three-dimensional region in the interior of the pore with the narrowest diameter. Depending on the length of the constriction zone, the number of polymer subunits that influence the passage of electrolytes, and thus the current output signal, can vary. The output signal produced by the nanopore system is any measurable signal that provides a multitude of distinct and reproducible signals depending on the physical characteristics of the polymer or polymer subunit(s). For example, the ionic current level through the pore is an output signal that can vary depending on the particular polymer subunit(s) residing in the constriction zone of the nanopore. As the polymer translocates in iterative steps (e.g., linearly, subunit by subunit through the pore), the current levels can vary to create a trace, or "current pattern," of multiple output signals corresponding to the contiguous sequence of the polymer subunits. This detection of current levels, or "blockade" events have been used to characterize a host of information about the structure polymers, such as DNA, passing through, or held in, a nanopore in various contexts.

In general, a "blockade" is evidenced by a change in ion current that is clearly distinguishable from noise fluctuations and is usually associated with the presence of an analyte molecule, e.g., one or more polymer subunits, within the nanopore such as in the constriction zone. The strength of the blockade, or change in current, will depend on a characteristic of the polymer subunit(s) present. Accordingly, in some embodiments, a "blockade" is defined against a reference current level. In some embodiments, the reference current level corresponds to the current level when the nanopore is unblocked (i.e., has no analyte structures present in, or interacting with, the nanopore). In some embodiments, the reference current level corresponds to the current level when the nanopore has a known analyte (e.g., a known analyte polymer subunit) residing in the nanopore. In some embodiments, the current level returns spontaneously to the reference level (if the nanopore reverts to an empty state, or becomes occupied again by the known analyte). In other embodiments, the current level proceeds to a level that reflects the next iterative translocation event of the polymer analyte domain through the nanopore, and the particular subunit(s) residing in the nanopore change(s). To illustrate, with respect to the reference current level defined as an unblocked level, the blockade is established when the current is lower than the reference current level by an amount of about 1-100% of the reference current level. It will be understood that the reference current level can immediately precede the blockade event or, alternatively, be separated from the blockade event by a period of time with intervening current measurements. For example, the ionic current may be lower than the reference current level by a threshold amount of about, at least about, or at most about 1%, 2%, 3%, 4%, 5%, 10%, 15%, 20%, 25%, 30%, 35%, 40%, 45%, 50%, 55%, 60%, 65%, 70%, 75%, 80%, 85%, 90%, 95%, or 100%, or any range derivable therein, of the reference current level when a polymer analyte domain subunit enters the nanopore. With respect to the reference current level defined by the presence of a known analyte (e.g., known polymer subunit(s)), the blockade is established when the current is lower or higher than the reference level by an amount of about 1-100% of the reference current level. It will be understood that the reference current level can immediately precede the blockade event or, alternatively, be separated from the blockade event by a period of time with intervening current measurements. For example, the ionic current may be lower or higher than the reference current level by threshold of about, at least about, or at most about 1%, 2%, 3%, 4%, 5%, 10%, 15%, 20%, 25%, 30%, 35%, 40%, 45%, 50%, 55%, 60%, 65%, 70%, 75%, 80%, 85%, 90%, 95%, or 100%, or any range derivable therein, of the reference current level when a polymer analyte domain subunit enters the nanopore. "Deep blockades" can be identified as intervals where the ionic current is lower (or higher) by at least 50% of the reference level. Intervals where the current drops by less than 50% of the reference level can identified as "partial blockades." In some embodiments, the current level in a blockade remains at the reduced (or elevated) level for at least about 1.0 µs.

In some embodiments, the measurable signal obtained from nanopore analysis of the polymer analyte domain is compared against a known signal or a signal obtained from a known analyte. The term "known analyte" is used in reference to an analyte for which the status with respect to a particular characteristic, such as subunit sequence, is known. In some embodiments, the known signal is obtained from the known analyte under the same or similar analytical conditions. In some embodiments, the comparison of measurable signals, such as current patterns obtained from an unknown analyte domain and a reference standard polymer analyte permits the identification of an identifiable "fingerprint" that distinguishes the analyte domain from other potential analyte domains. In some embodiments, the comparison of measurable signals, such as current patterns obtained from an unknown analyte domain and a reference standard polymer analyte permits the identification of one or more polymer subunits in the analyte domain. It will be understood that in these embodiments, the current levels of corresponding polymer subunit identities in the unknown and reference analyte polymer domains do not have to match. Instead, the identities can be determined by their relative current levels among current levels corresponding to a finite selection of subunit identities.

In another aspect, the present disclosure provides a method of increasing the interaction rate between a polymer and a nanopore disposed between a first conductive liquid medium and a second conductive liquid medium. The method comprises applying an electric field sufficient to translocate a polymer having an analyte domain and an end domain from the first conductive liquid medium to the second conductive liquid medium through the nanopore. In some embodiments, the method also comprises measuring an ion current to provide a current pattern, wherein a difference in the ion current from a threshold ion current level in the current pattern, as described above, indicates an interaction between the polymer and the nanopore.

Various elements relating to this aspect of the disclosure, such as polymer analytes, the polymer end domain, the polymer analyte domain, the at least one (i.e., "first") charged moiety, nanopores and nanopore systems, ion currents and current patterns, etc., are described in more detail above with respect to other aspects of the invention. The aforementioned descriptions, however, apply equally to the present aspect of the invention.

As used herein, the term "interaction" refers to the contact or close association of any part of a polymer analyte with the nanopore. In preferred embodiments, an end domain of the polymer analyte interacts with the nanopore. With the application of an electrical field, the polymer analyte in the first conductive liquid medium will eventually interact with the nanopore. To successfully analyze the polymer analyte, an end domain of the analyte must first come into close association with the outer rim of the nanopore (e.g., such as on the cis side of the nanopore). In some embodiments, the interaction event comprises the polymer end domain entering into the interior space defined by the vestibule of the nanopore. As described in more detail below, the addition of charged moieties (e.g., phosphate groups) to the end domain of a polymer analyte substantially increased the rate at which the polymer analyte interacted with the nanopore, as evidenced by measurable current blockades. The increased interaction rate, in turn facilitates a much more efficient analysis of polymers. This is especially advantageous for very long polymer analytes or analytes of low copy number, which might not otherwise have an end domain that will likely interact with the nanopore, even with the application of an electrical field.

Accordingly, the application of the present disclosure provides for an enhanced, or increased, interaction rate between a polymer analyte and nanopore. In some embodiments, the interaction rate between the nanopore and the polymer is at least 10%, 20%, 30%, 40%, 50%, 60%, 70%, 80%, 90%, 100%, 150%, 200% or more, higher than the interaction rate between the nanopore and a similar polymer lacking the first charged moiety in the end domain. In some embodiments, the similar polymer lacking the first charged moiety in the end domain is the same type of polymer (e.g., polypeptide, DNA, RNA, PNA etc.). In some embodiments, the similar polymer lacking the first charged moiety in the end domain has a length that is between at least 80% and 120% of the length of the polymer analyte. In some embodiments, the similar polymer lacking the first charged moiety in the end domain has a subunit sequence that is at least 80%, 85%, 90%, 95%, or 99% identical to the polymer analyte.

In another aspect, the disclosure provides a method of sequencing two or more nucleotides of a nucleic acid, comprising: (a) providing a nucleic acid comprising at least two unknown nucleotides in an analyte domain, the nucleic acid further comprising a positively or negatively charged moiety in an end domain at the 3' or 5' end; (b) providing a porin positioned between a cis side, comprising a first conductive liquid medium and the modified nucleic acid, and a trans side, comprising a second conductive liquid medium; and (c) causing the nucleic acid to pass through a tunnel of the porin, thereby producing a first and a second ion current level, thereby sequencing two or more nucleotides of the nucleic acid.

In another aspect, the disclosure provides a method of improving the rate and efficiency of nanopore sequencing of an analyte, comprising: (a) providing a nanopore positioned between a cis side comprising a first conductive liquid medium and an analyte modified with one or more positive or negative charged moieties in an end domain on the 3' or 5' end, and a trans side comprising a second conductive liquid medium, wherein the nanopore comprises an opening that provides liquid communication between the cis side and the trans side; (b) causing the modified analyte to enter an opening in the nanopore, thereby producing a measurable ion current level, wherein the ion current level represents a first known unit of the analyte; (c) advancing the modified analyte toward the trans side, thereby producing a second ion current level representing a second unit; and (e) calibrating the nanopore with a known modified analyte containing all units and corresponding ion current levels of interest and thereby correlating each ion current level with a known unit of an analyte. This or any other method may be repeated to sequence a third, fourth, fifth, etc., known unit in the modified analyte.

In another aspect, the present disclosure provides a polymer adapter composition. The adapter comprises a polynucleic acid and a charged moiety linked to at least one of the nucleotides in the polynucleic acid.

In some embodiments, the charged moiety is covalently linked to at least one of the nucleotides in the polynucleic acid.

In some embodiments, the polynucleic acid adapter is between 1 and 20 nucleotides in length. For example, embodiments include an adapter with a polynucleic acid with 1, 2, 3, 4, 5, 6, 7, 8, 9, 10, 11, 12, 13, 14, 15, 16, 17, 18, 19, or 20 nucleotides.

In some embodiments, the charged moiety in the adapter composition comprises at least two phosphate groups, at least two sulfate groups, or at least one phosphate group and one sulfate group. In some embodiments, the adapter composition comprises four groups, wherein each group is independently selected from a phosphate or sulfate.

In some embodiments, the phosphate group(s) and/or sulfate group(s) are arranged in linear configuration. In some embodiments, the phosphate group(s) and/or sulfate group(s) are arranged in a branched ("doubler") configuration, as described herein.

In some embodiments, the charged moiety is linked to a nucleotide that is within 3 residue positions of a terminal nucleotide (i.e., either the 5' or 3' terminal nucleotide). In some embodiments, the charged moiety is linked to a terminal nucleotide. In some embodiments, the charged moiety is linked to the 3' terminal nucleotide. In some embodiments, the charged moiety is linked to the 5' terminal nucleotide.

The adapter composition is useful as a reagent that can be added to the ends of unknown analyte sequences to facilitate nanopore-based analysis thereof. For example, an adapter comprising a short oligonucleotide sequence and a charged moiety at the 5' end can be ligated to the 5' end of a nucleotide polymer of unknown sequence. Specifically, the 3' end of the adapter (the end without an added charged moiety) is ligated to the 5' end of the nucleotide polymer of unknown sequence. In this example, the adapter with the charged moiety serves as the end domain of the final nucleotide analyte construct, whereas the nucleotide polymer of unknown sequence serves as the analyte domain of the final nucleotide analyte construct, in accordance with the above description.

In another aspect, the present disclosure provides a kit comprising the adapter composition described above. In some embodiments, the kit is useful for nanopore-based polymer sequencing. In some embodiments, the kit further comprises reagents to facilitate the ligation of the adapter to the polymer to be analyzed (i.e., the analyte domain). In some embodiments, the kit further comprises elements of the nanopore system, described above. For example, the kit can further comprise structural elements such as a nanopore, a multi-chamber assay container in which the nanopore can be installed between conductive liquid media, and apparatus for applying and measuring electric fields.

The use of the term "or" in the claims is used to mean "and/or" unless explicitly indicated to refer to alternatives only or the alternatives are mutually exclusive, although the disclosure supports a definition that refers to only alternatives and "and/or."

Following long-standing patent law, the words "a" and "an," when used in conjunction with the word "comprising" in the claims or specification, denotes one or more, unless specifically noted.

Unless the context clearly requires otherwise, throughout the description and the claims, the words 'comprise,' 'comprising,' and the like are to be construed in an inclusive sense as opposed to an exclusive or exhaustive sense; that is to say, in the sense of "including, but not limited to." Words using the singular or plural number also include the plural and singular number, respectively. Additionally, the words "herein," "above," and "below," and words of similar import, when used in this application, shall refer to this application as a whole and not to any particular portions of the application.

Disclosed are materials, compositions, and components that can be used for, can be used in conjunction with, can be used in preparation for, or are products of the disclosed methods and compositions. It is understood that, when combinations, subsets, interactions, groups, etc., of these materials are disclosed, each of various individual and collective combinations is specifically contemplated, even though specific reference to each and every single combination and permutation of these compounds may not be explicitly disclosed. This concept applies to all aspects of this disclosure including, but not limited to, steps in the described methods. Thus, specific elements of any foregoing embodiments can be combined or substituted for elements in other embodiments. For example, if there are a variety of additional steps that can be performed, it is understood that each of these additional steps can be performed with any specific method steps or combination of method steps of the disclosed methods, and that each such combination or subset of combinations is specifically contemplated and should be considered disclosed. Additionally, it is understood that the embodiments described herein can be implemented using any suitable material such as those described elsewhere herein or as known in the art.

Publications cited herein and the subject matter for which they are cited are hereby specifically incorporated by reference in their entireties.

The following is a description of an exemplary approach for improving the interaction rate between a polymer analyte and a nanopore by adding a charged moiety at an end domain.

The M2-MspA protein was generated from *Mycobacterium smegmatis* as previously described in Butler, T. Z., Pavlenok, M., Derrington, I. M., Niederweis, M., and Gundlach, J. H., "Single-molecule DNA detection with an engineered MspA protein nanopore," *Proc. Natl. Acad. Sci. USA* 105:20647-20652 (2008), which is incorporated herein by reference in its entirety. Specifically, M2-MspA protein contains mutations D90N/D91N/D93N/D118R/E139K/D134R with reference to the wild-type MspA protein. The DNA oligonucleotides were synthesized at Stanford University Protein and Nucleic Acid Facility and purified using column purification methods. DNA templates, primers and blocking oligomers were mixed at relative molar concentrations of 1:1:1.2 and annealed by incubating at 95° C. for 3 min followed by slow-cooling to below 30° C. DNA and phi29 DNAP were stored at −20° C. until immediately before use.

Single MspA pores were established in a lipid bilayer with previously described methods in Butler, T. Z., et al., *Proc. Natl. Acad. Sci. USA* 105:20647-20652 (2008). Briefly, 1,2-diphytanoyl-sn-glycerol-3-phosphocholine (Avanti Polar Lipids, Alabaster AL) lipid bilayers were formed across a horizontal ~20 µm diameter Teflon aperture. The 60 µl compartments on both sides of the bilayer contained experimental buffer of 0.3 M KCl, 1 mM EDTA, 1 mM DTT, and 10 mM HEPES/KOH buffered at pH 8.0±0.05. An Axopatch 200B integrating patch clamp amplifier (Axon Instruments) applied a 180 mV voltage across the bilayer (trans side positive) and measured the ionic current through the pore. The M2-MspA was added to the grounded cis compartment, yielding a concentration of ~2.5 ng/ml. Once a single pore inserted, the compartment was flushed with experimental buffer to avoid further insertions.

Figure 1A:
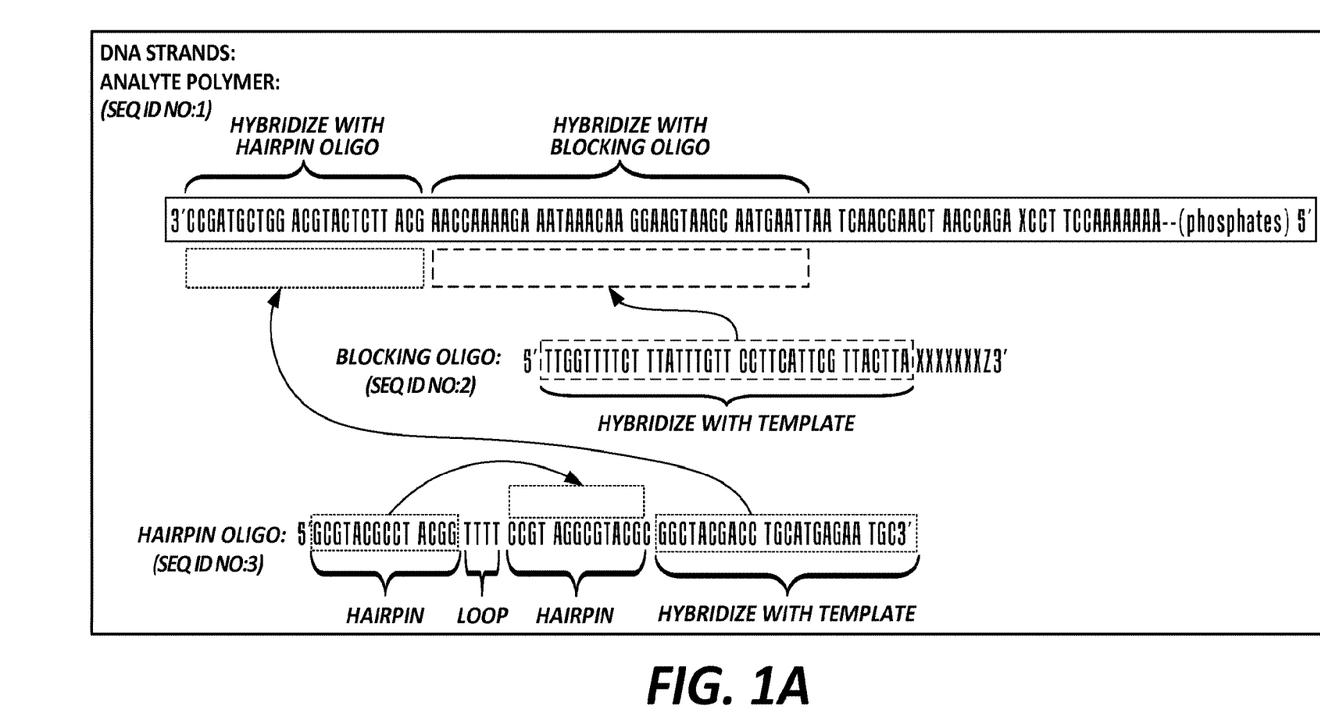
FIGS. 1A and 1B illustrate a DNA analyte polymer with a phosphate group attached to the 5' terminal end, according to one embodiment of the invention. Specifically.
Figure 1B:
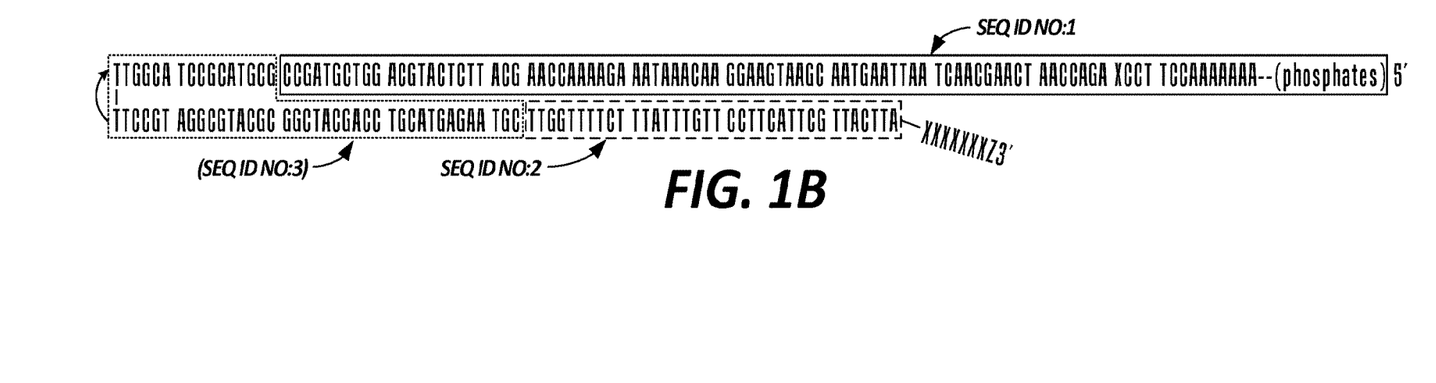

The analyte polymers were prepared in a manner to translocate through the MspA nanopore in association with the molecular motor phi29, as described in Manrao et al., "Reading DNA at single-nucleotide resolution with a mutant MspA nanopore and phi29 DNA polymerase," *Nat. Biotechnol.* 30:349-353 (2012), incorporated herein by reference. Briefly, ssDNA analytes were prepared with 3' sequence domains that anneal to a blocking oligo and a separate hairpin oligo, as illustrated in FIG. 1A. In all experiments, 80-91 nucleotide (nt) DNA strands (exemplified by SEQ ID NO:1) containing the section to be read (i.e., the "analyte domain") were annealed to a "hairpin oligo" primer complementary to the 2 nucleotides at the template's 3' end. The sequence set forth in SEQ ID NO:1 contains an "n" residue at position 14, which represents an X, or an abasic residue. This abasic position can be used to confirm the positioning of the analyte in the nanopore and to correspond with the current levels measured as the analyte passes through the nanopore. It will be understood, however, that this feature is not required in the analyte polymer for the present invention to function. The hairpin oligo primer (exemplified by SEQ ID NO:3) had a sequence on its respective 5' end to allow it to fold on itself and prevent the phi29 DNAP from acting on the double stranded end of the DNA analyte construct. Adjacent to the hairpin primer as annealed to the analyte domain, a blocking oligomer was annealed. The blocking oligomer (exemplified by SEQ ID NO:2) contained a sequence complementary to an interior domain of the analyte strand and adjacent to the sequence complementary to the hairpin oligo. The blocking oligo also contained, at its 3' end, an "abasic fray" domain with seven abasic residues and a three-carbon spacer. The abasic positions and carbon spacers are indicated in FIGS. 1A and 1B with X and Z, respectively.

The blocking oligo functions to prevent phi29 DNA polymerase ("DNAP") synthesis from taking place in bulk solution. The association of the blocking oligo with the DNA analyte strand restricts the action of phi29, such that it can only ratchet the DNA analyte through when the DNA analyte strand has been fed into the desired pore. When the DNA-phi29 DNAP conjugate is pulled into the pore, the force of the pore on the phi29 DNAP pushes it into the blocking oligo, effectively unzipping the blocking oligo from the analyte strand in single nucleotide steps. This unzipping permits an initial read of the template DNA strand as it is fed through the pore at a sustainable rate. Once the blocking oligo is fully unzipped and disassociated from the analyte strand, the 3' end of the hairpin oligo is exposed to the phi29 polymerase's active site and DNA synthesis takes place. The template strand is pulled out of the pore and a second read is made as the strand passes through the pore in the opposite direction. See, e.g., Manrao et al., "Reading DNA at single-nucleotide resolution with a mutant MspA nanopore and phi29 DNA polymerase," *Nature Biotechnology* 30:349-353 (2012), incorporated herein by reference in its entirety.

The analyte polymers contained a charged moiety that was added at the 5' end (or not, for control). Different moieties comprised 1, 2, or 4 phosphate groups. The moieties with two or more phosphates incorporated one or more branching, or "doubler," conformations as described above. It will be understood that a variety of phosphate configurations, with or without doublers, can incorporated into synthetic oligos. In cases where unknown analytes, such as genomic DNAs, are to be analyzed, the synthetic oligos with the phosphates (i.e., end domains) can be ligated to the unknown analyte The annealed DNA hairpin constructs, as shown in FIG. 1B, were then added to the experimental cis volume to achieve a final concentration near ~1 µM. As described, a single MspA pore had been inserted into a lipid bilayer separating two chambers (cis and trans) containing 0.3 M KCl buffer solution. A patch-clamp amplifier was applied +180 mV to the trans side of the bilayer and was used measured the ionic current through the pore. The current through an open MspA pore was Io=110±6 pA (mean±s.d., N=25). Once the hairpin DNA was added to the system interactions were observed between the DNA analyte and the pore as previously described in Butler, T. Z., et al., *Proc. Natl. Acad. Sci. USA* 105:20647-20652 (2008). Mid-states were associated with DNA entering the nanopore vestibule while deep-states (indicated by current levels dropping by 40%, or dropping to a level that was 60% of the unblocked, open pore current) were associated with the DNA threading through the pore and translocating through to the other side.

Figure 2:
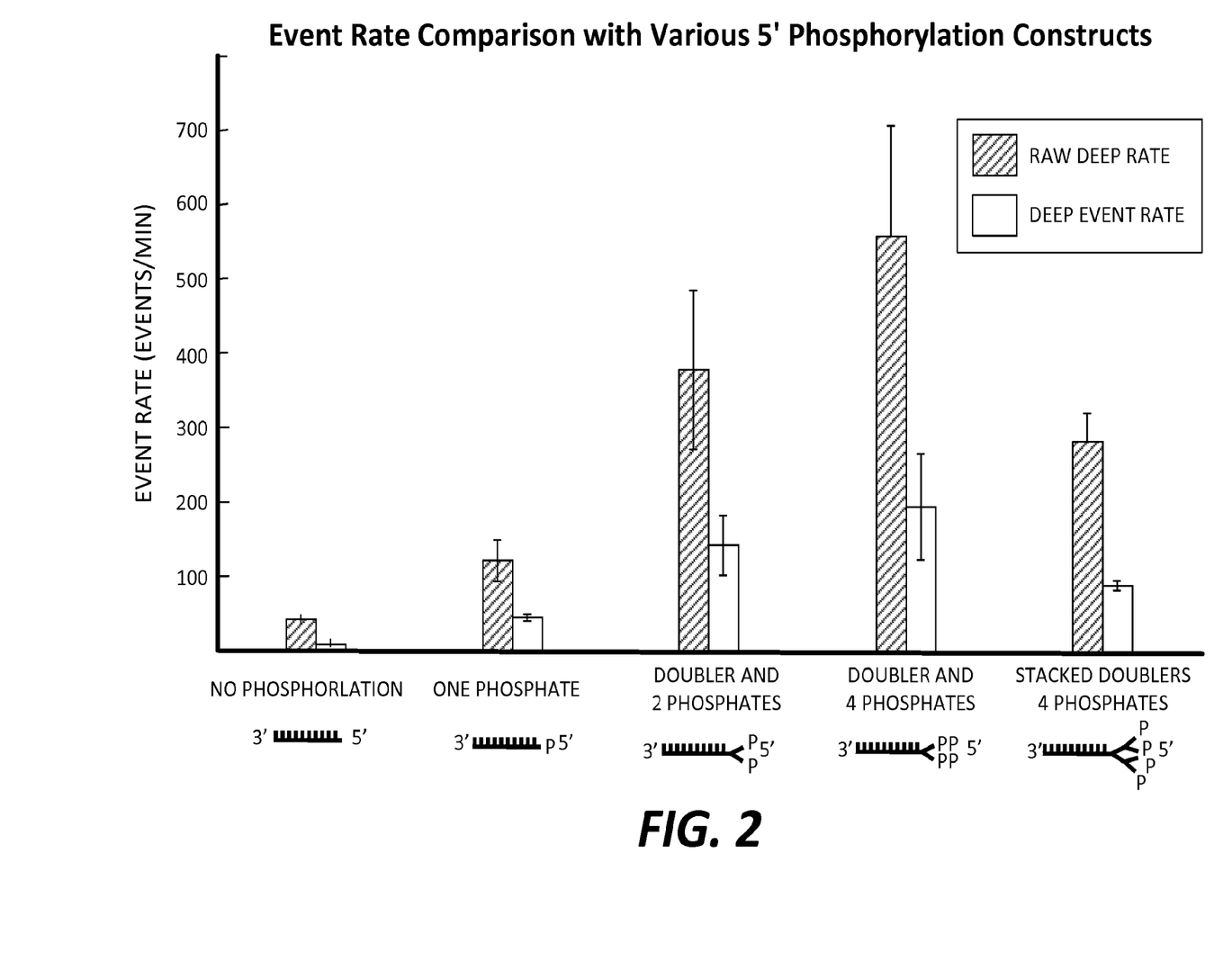
FIG. 2 illustrates the effect of increasing negative charges on nucleic acid-pore interaction rates. The event rate is illustrated for a template DNA analyte strand that contains no or increasing numbers of phosphate groups in various illustrated configurations at the 5' terminal end. "Raw" events are associated with any measurable interaction between the nucleic acid and the pore, whereas "deep" events are the proportion of "raw" events that are associated with nucleic acid translocation through the pore. The illustrated charged moieties are demonstrated as enhancing nucleic acid-pore interaction rate well above nucleic acid without phosphorylation. The charged moieties with multiple phosphate groups were generated with an asymmetric doubler configuration.

The addition of the charged moiety, i.e., phosphorylation resulted in a significant increase in both mid-state event rates and, more importantly, deep-state event rates. The "raw event rate," which includes all instances of measured mid- and deep-states, and the "deep event rate" are illustrated in FIG. 2 for the analyte constructs with different charged moieties.

Figure 3:
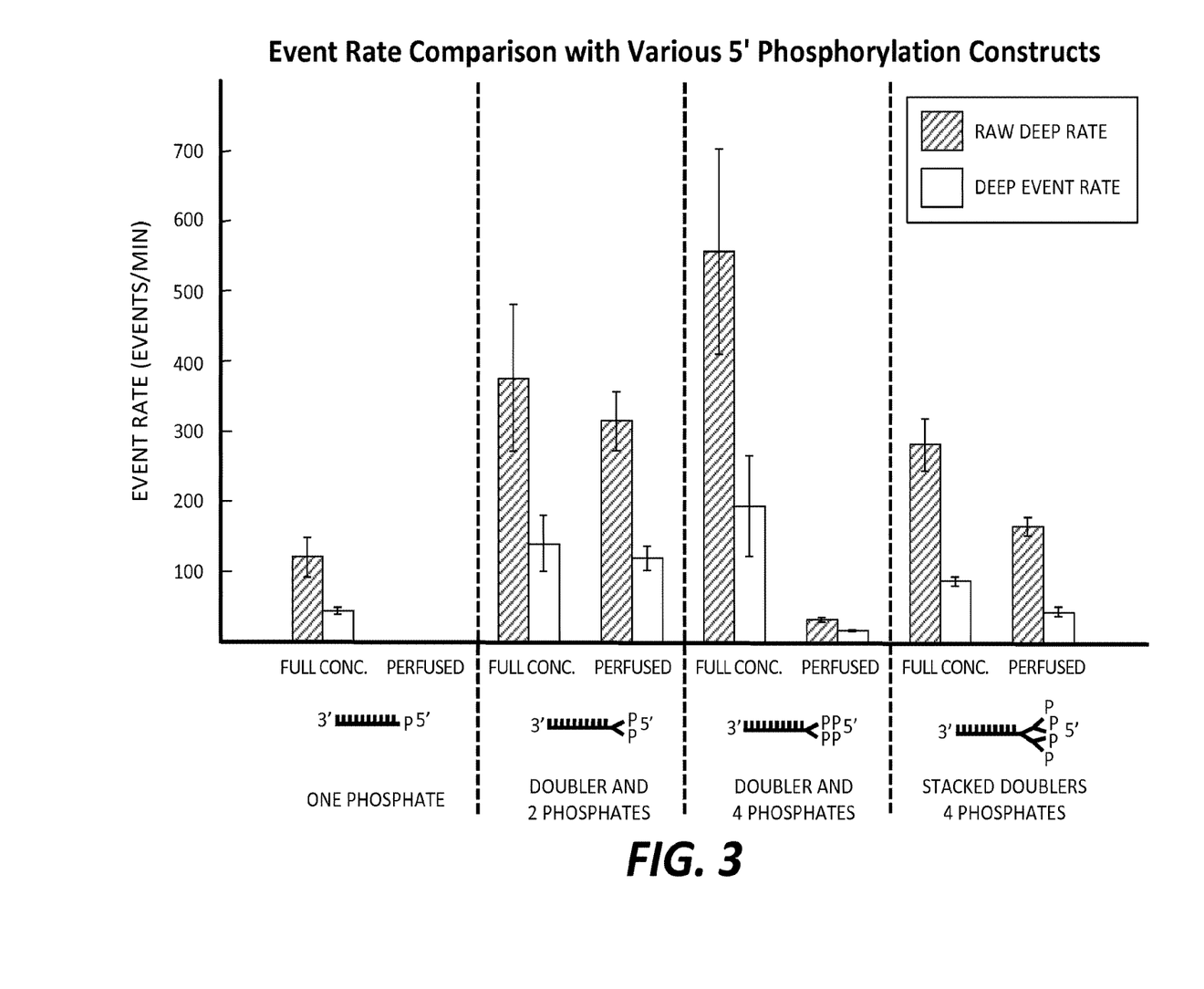
FIG. 3 illustrates that DNA analyte polymers having a variety of negative charged moieties, such as asymmetric doublers and/or phosphorylation, have varying degrees of adherence of DNA to the cis volume, even after perfusion.

FIG. 3 illustrates the effect of perfusion on the analyte-nanopore interaction rate. During perfusion, the cis well buffer was replaced by flowing new buffer into the cis well with a syringe, while removing buffer from the cis well with a second syringe. Generally, the perfusion procedure removes the majority of analytes without added charged moieties. See, e.g., FIG. 3, left column. In contrast, analytes with phosphate moieties were less easily perfused. Without being bound to any particular theory, it is possible that the additional negative charge on the DNA analytes facilitates association with the nanopore and/or lipid bilayer. Such interaction might allow for aggregation of the analytes near to the pore, thus contributing to the increased analyte-nanopore interaction rates.

In conclusion, these data demonstrate that the addition of a charged moiety at an end of a DNA polymer analyte significantly enhances the interaction rate between the DNA analyte and the nanopore. This increased interaction rate also correlates with a significantly increased translocation rate, which can lead to significantly improved analysis conditions, such as increased sequencing performance.

While illustrative embodiments have been illustrated and described, it will be appreciated that various changes can be made therein without departing from the spirit and scope of the invention.

The invention claimed is:

1. A polymer adapter composition, comprising:
   a polynucleic acid with between 1 and 20 nucleotides,
   a charged moiety linked to a terminal nucleotide of the polynucleic acid,
   wherein the charged moiety comprises one of: at least two phosphate groups arranged in linear and/or branched configuration, and a sulfate group, and wherein the polynucleic acid is configured to be ligated to a terminal end of a nucleic acid polymer analyte.

2. The composition of claim 1, comprising at least two sulfate groups arranged in linear and/or branched configuration.

3. The composition of claim 2, wherein the sulfate groups are disposed in a branched configuration with two or more charged groups in each branch.

4. The composition of claim 1, wherein the phosphate groups are disposed in a branched configuration with two or more charged groups in each branch.

5. The composition of claim 1, wherein the charged moiety comprises at least one phosphate and at least one sulfate.

6. The composition of claim 5, wherein the at least one phosphate and at least one sulfate are arranged in linear and/or branched configuration.

7. The composition of claim 1, wherein the charged moiety is linked to a nucleotide that is within three residue positions of a terminal nucleotide of the polynucleic acid.

8. The composition of claim 1, wherein the terminal nucleotide of the polynucleic acid is the 5' terminal nucleotide.

9. The composition of claim 1, wherein the terminal nucleotide of the polynucleic acid is the 3' terminal nucleotide.

10. The composition of claim 1, wherein the charged moiety increases the energetic favorability for the polynucleic acid to interact with a nanopore comprising an opening or vestibule with a net positive charge.

11. A kit for nanopore-based polymer sequencing, comprising the adapter composition of claim 1.

12. The kit of claim 11, further comprising reagents for ligating the adapter to a polymer analyte domain.

13. The kit of claim 11, further comprising a nanopore system.

14. The kit of claim 13, wherein the nanopore system comprises a nanopore, a multi-chamber assay container, apparatus for applying and measuring electric fields, a molecular motor that translocates a polymer through the nanopore enzymatically, or any combination thereof.

15. The kit of claim 14, wherein the nanopore is a protein nanopore with a tunnel structure comprising a vestibule and a constriction zone, and wherein the vestibule and/or constriction zone has a net positive charge.

* * * * *

UNITED STATES PATENT AND TRADEMARK OFFICE
CERTIFICATE OF CORRECTION

| | | |
|---|---|---|
| PATENT NO. | : 11,821,033 B2 | Page 1 of 1 |
| APPLICATION NO. | : 17/111167 | |
| DATED | : November 21, 2023 | |
| INVENTOR(S) | : J. Gundlach et al. | |

It is certified that error appears in the above-identified patent and that said Letters Patent is hereby corrected as shown below:

On the Title Page

| | | |
|---|---|---|
| Item (57)/Abstract | Line 9 | change "also provide" to -- also provides -- |
| Item (57)/Abstract | Line 12 | change "to an" to -- to a -- |

Signed and Sealed this
Twentieth Day of January, 2026

John A. Squires
*Director of the United States Patent and Trademark Office*